United States Patent
Gallo, Jr.

(10) Patent No.: US 10,337,979 B1
(45) Date of Patent: Jul. 2, 2019

(54) DEVICE FOR HOLDING A COUPON AND COLLECTING A SAMPLE OF A FLUID

(71) Applicant: Jose Gallo, Jr., Midland, TX (US)

(72) Inventor: Jose Gallo, Jr., Midland, TX (US)

(*) Notice: Subject to any disclaimer, the term of this patent is extended or adjusted under 35 U.S.C. 154(b) by 224 days.

(21) Appl. No.: 15/666,251

(22) Filed: Aug. 1, 2017

Related U.S. Application Data

(63) Continuation-in-part of application No. 13/862,838, filed on Apr. 15, 2013, now abandoned.

(51) Int. Cl.
| | |
|---|---|
| *G01N 17/04* | (2006.01) |
| *G01N 1/34* | (2006.01) |
| *B01D 29/15* | (2006.01) |
| *B01D 35/02* | (2006.01) |
| *B01D 35/30* | (2006.01) |

(52) U.S. Cl.
CPC .......... *G01N 17/046* (2013.01); *B01D 29/15* (2013.01); *B01D 35/02* (2013.01); *B01D 35/306* (2013.01); *G01N 1/34* (2013.01); *B01D 2201/0415* (2013.01)

(58) Field of Classification Search
None
See application file for complete search history.

(56) References Cited

U.S. PATENT DOCUMENTS

| | | | |
|---|---|---|---|
| 4,697,465 A | 10/1987 | Evans | |
| 4,734,194 A * | 3/1988 | Kalman | B01D 35/043 137/547 |
| 4,734,197 A | 3/1988 | Kalman et al. | |
| 4,859,610 A | 8/1989 | Maggio | |
| 5,150,065 A | 9/1992 | Luna | |
| 2002/0194905 A1 | 12/2002 | Moghissi | |
| 2004/0079236 A1 * | 4/2004 | Welker | B01D 46/0031 96/413 |
| 2008/0245717 A1 | 10/2008 | Heikamp | |

* cited by examiner

*Primary Examiner* — Matthew D Krcha
(74) *Attorney, Agent, or Firm* — Rao DeBoer Osterrieder, PLLC; Dileep P. Rao

(57) ABSTRACT

A device for holding a coupon and collecting a sample of a fluid. The device is for use in a pipeline. The device reduces solids that contact the coupon. The device has a filter housing having a filter screen operatively located thereon, wherein the coupon is located within the filter housing, and wherein a screen is operatively disposed about the coupon.

14 Claims, 2 Drawing Sheets

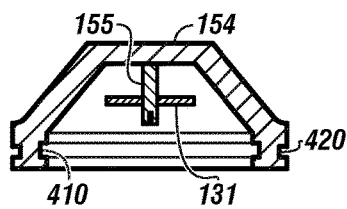
FIGURE 4
FIGURE 5
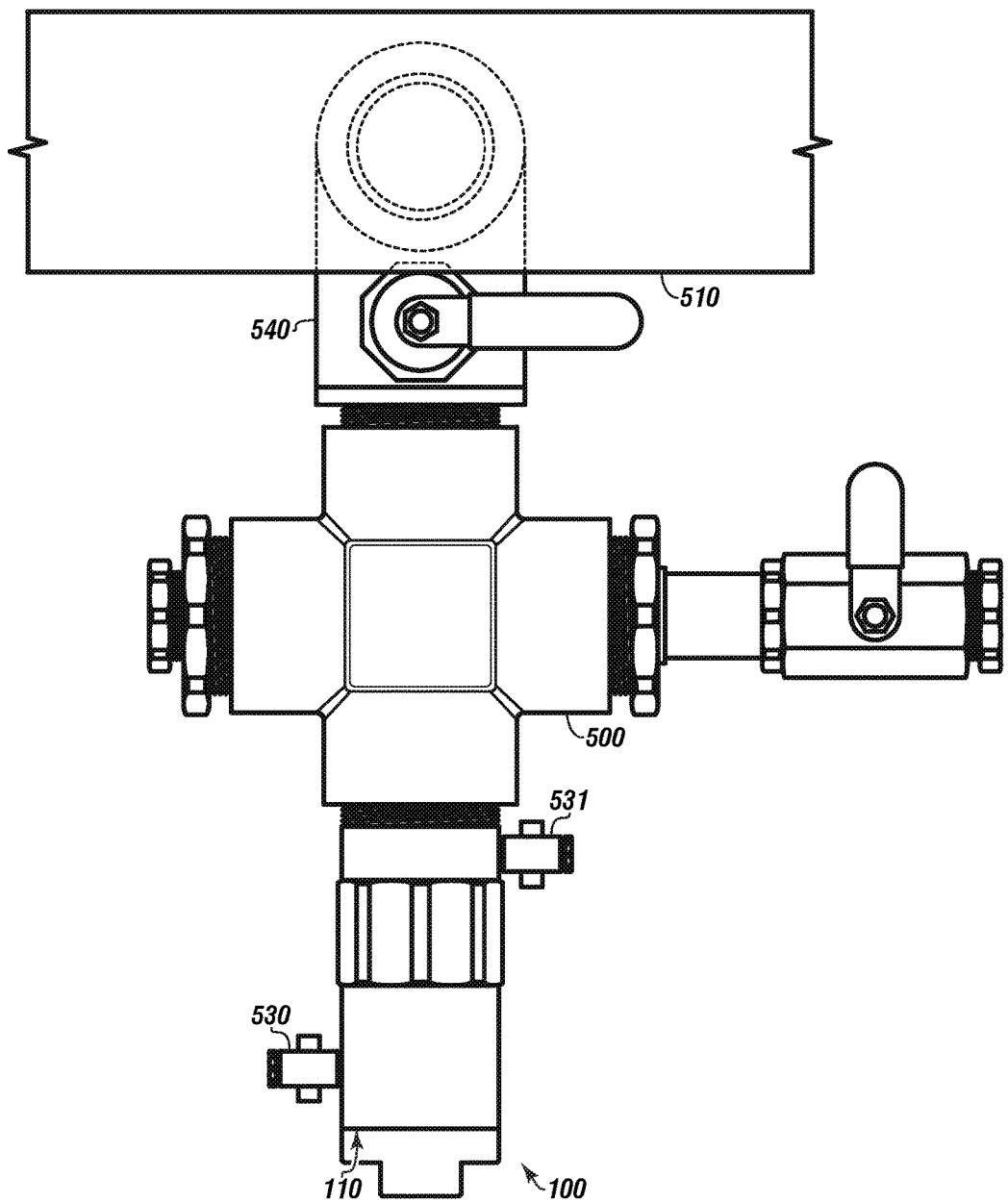

DEVICE FOR HOLDING A COUPON AND COLLECTING A SAMPLE OF A FLUID

CROSS REFERENCE TO RELATED APPLICATIONS

The present application is a Continuation in Part of co-pending U.S. patent application Ser. No. 13/862,838 filed on Apr. 15, 2013, titled "DEVICE FOR HOLDING A COUPON AND COLLECTING A SAMPLE OF A FLUID". This reference is incorporated herein in its entirety.

BACKGROUND

Fluids being transported via a pipeline often cause corrosion to pipes and other pipe fittings in use. It is desirable to measure the corrosivity of the fluid being pumped. One type of corrosion is due to bacterial growth in water or other fluids being pumped. Microbial corrosion, also known as bacterial corrosion, bio-corrosion, microbiologically influenced corrosion, or microbially induced corrosion (MIC), is caused or promoted by microorganisms such as chemoautotrophs.

One method of measuring corrosivity of a fluid is to install a monitoring device containing a "coupon" and monitor the corrosion of the coupon. A specific area of interest is where water settles to the bottom.

It is desirable to measure corrosion rates at low lying areas of the pipe. For example, in crude oil and wet gas systems, the water space (or the water separation area) is the most corrosive environment, and water would tend to collect in the low-lying areas of the pipeline.

However, it is often not feasible to measure at such locations due to space constraints, or other limitations. For example, if a pipe is routed underneath a roadway, it is desirable to measure corrosion under the roadway, but not practical to do so.

Further, maintenance procedures, such as pigging a pipeline can result in solids collecting at monitoring devices, and providing a false high "metal loss" reading. Solids collecting, contacting, and/or compacting the coupon can cause a higher than actual corrosivity reading.

A need exists for a device for holding a coupon and collecting a sample of a fluid which mimics a low-lying area of the pipeline in order to measure expected corrosivity of the fluid which can allow for bacterial growth.

A need also exists for a device for holding a coupon and collecting a sample of a fluid that reduces the solids that contact a coupon.

A further need exists for a device for holding a coupon and collecting a sample of fluid that does not have any metallic parts contacting the coupon in order to get a true corrosivity reading.

The present disclosure meets these needs.

BRIEF DESCRIPTION OF THE DRAWINGS

The detailed description will be better understood in conjunction with the accompanying drawings as follows:

FIG. 4 depicts a detailed view of a retainer configured to snap into the filter housing of FIG. 2.

FIG. 5 depicts the device for holding a coupon and collecting a sample of a fluid installed on a pipeline according to one or more embodiments.

Figure 3:
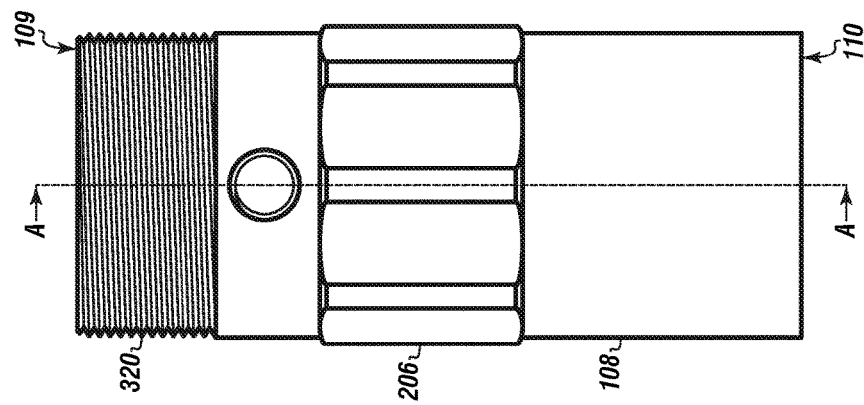
FIG. 3 depicts the outside of the filter housing according to one or more embodiments.

The present embodiments are detailed below with reference to the listed Figures.

DETAILED DESCRIPTION OF THE EMBODIMENTS

Before explaining the present invention in detail, it is to be understood that the invention is not limited to the specifics of particular embodiments as described and that it can be practiced, constructed, or carried out in various ways.

While embodiments of the disclosure have been shown and described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present invention.

Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description herein, but is only limited by the claims which follow, encompassing all equivalents of the subject matter of the claims. Each and every claim is hereby incorporated into the specification as an embodiment of the present disclosure. Thus, the claims are a further description and are an addition to the embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The present embodiments generally relate to a device for holding a coupon and collecting a sample of a fluid.

Pipeline, as used herein, can refer to any fluid transport pathway, whether used within an enclosed system or for transport from one location to another.

Coupon, as used herein, refers to a piece of material representative of the material desired to be tested. A corrosion coupon is a simple yet effective tool for providing a quantitative estimation of corrosion rates occurring in an operating system. They can also provide a visual indication of the type of corrosion which may be occurring in the monitored system. The coupon is immersed in or exposed to the fluid within the pipeline to enable estimation of the corrosion occurring during a specific set of conditions which, typically, mimic the conditions within the pipeline. Persons having ordinary skill in the art will be aware that coupon weight before and after service, in combination with a visual inspection will provide important pipeline corrosion information.

The coupon can be removably disposed within the device. In embodiments, the coupon is removable and replaceable.

The device for holding a coupon and collecting a sample of a fluid, also referred to as the device herein for brevity, can be used with a pipeline. The device can reduce the solids that contact the coupon by using a novel arrangement of filters.

The device can include a filter housing. In embodiments, the outer surface of the filter housing can have flat portions. The flat portions can allow a tool to engage the filter housing. The tool can be used to remove the device from a pipeline or an attachment connecting the device with the pipeline. The filter housing can have a filter screen receiver on a first end, and a second end configured to receive a sediment plug.

A filter screen can be placed in the filter screen receiver. The filter housing can have one or more holes formed therethrough in the filter screen receiver. The filter screen receiver can support the filter screen and maintain the filter screen in a desired position.

A retainer can be located in the filter screen receiver and can secure the filter screen therein. The retainer can snap or otherwise connect to the filter housing. The retainer does not comprise an opening through the retainer and the retainer is configured to keep the filter screen in an operative position on the first housing end. Further, the retainer seals the first housing end closed. The retainer can be made from any material. For example, the retainer can be nonmetallic.

One or more coupons can be operatively disposed within a cavity of the filter housing. The coupon can be any known in the art. In embodiments, multiple coupons of the same or different materials can be utilized. A screen can be aligned with the coupon to prevent solids from contacting the coupon. A filter cap can be connected with a first end of the screen, and a filter base adapter can be connected with a second end of the screen. The filter base adapter and the filter cap can be made from any material. For example, the filter base adapter and the filter cap can be nonmetallic.

The coupon can be connected with the filter base adapter in any known manner. For example, the coupon can have a threaded connecting with the filter base adapter. The filter base adapter can also be connected with the sediment plug in any manner known to persons having ordinary skill in the art.

A first opening can be formed through a side of the filter housing on an upper portion thereof, and a second opening can be formed through a side of the filter housing on a lower portion thereof. The first opening can be configured to provide ventilation to allow fluid to be drained out of the second opening. A valve can be located in or connected with the second opening. The valve can be selectively opened to allow fluid to flow out of the second opening.

A coupon guard can be disposed between the screen and the coupon. The coupon guard can be connected with the filter base adapter. The coupon guard can be made from any material. For example, the coupon guard can be nonmetallic.

The device can be disposed underneath a fluid flow pathway to mimic low-lying areas of the pipeline or system. The device can be placed at the "six o'clock" position, i.e. directly below the fluid flow pathway, to allow simulation of the most corrosive environment within the system.

The various screens and filtering mechanisms discussed allow for a more "true" reading of corrosivity within the pipeline. Solids suspended or dispersed within the pipeline fluid will not cause an erroneous corrosion measurement by utilizing the coupon.

Figure 1:
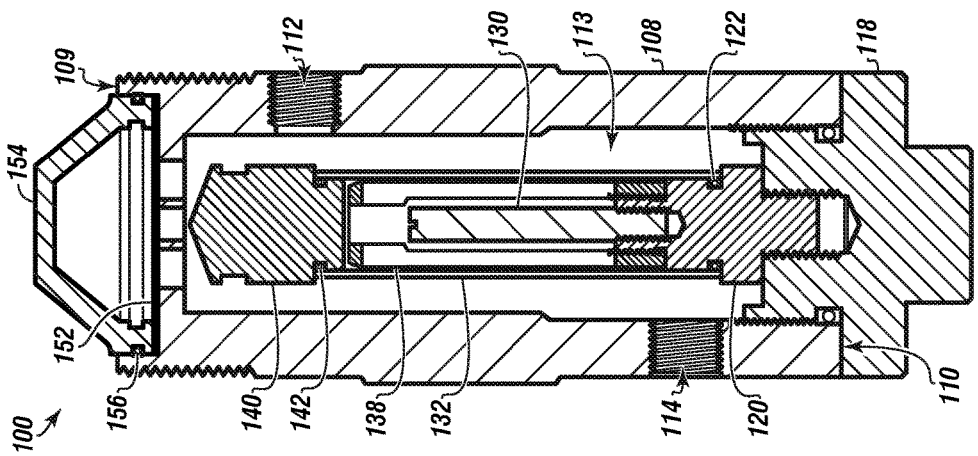
FIG. 1 depicts a device for holding a coupon and collecting a sample of a fluid according to one or more embodiments.

Turning now to the Figures, FIG. 1 depicts an embodiment of a device for holding a coupon and collecting a sample of a fluid according to one or more embodiments.

The device 100 can include a filter housing 108. The filter housing 108 can be made from any material. The filter housing 108 can have any shape. The filter housing 108 can have a first housing end 109 and a second housing end 110. The first housing end 109 can have a diameter that is different from or the same as a diameter of the second housing end 110. The filter housing 108 can have a cavity 113 formed therein. The cavity 113 can have any shape.

A first opening 112 can be formed through a side of the filter housing 108 on an upper portion thereof, such as proximate to the first housing end 109. The first opening 112 can provide ventilation to the cavity 113 to allow fluid in the cavity 113 to drain out of a second opening 114. The second opening 114 can be formed through a side of the filter housing 108 on a lower portion thereof, such as proximate the second housing end 110. A valve can be connected with the second opening 114. The valve can be selectively operated to allow fluid to drain out of the cavity 113. The fluid can be collected and analyzed.

A coupon 130 can be located within the cavity 113. The coupon 130 can be concentrically aligned with a screen 132. A filter cap 140 can be connected with a first end of the screen 132. A first seal device 142 can be disposed between the filter cap 140 and the screen 132. The first seal device 142 can be any sealing device. Illustrative sealing devices include O-rings, gaskets, or similar devices. A coupon guard 138 can have a top portion located between the filter cap 140 and the coupon 130. The coupon guard 138 can extend down between the screen 132 and the coupon 130. The coupon guard 138 can secure at a lower portion to a filter base adapter 120.

The filter base adapter 120 can connect with a second end of the screen 132. The filter base adapter 120 can also connect with the coupon 130. A second seal device 122 can be disposed between the filter base adapter 120 and the screen 132. The second seal device 122 can be any sealing device. Illustrative sealing devices include O-rings, gaskets, or similar devices.

A filter screen 152 can be located on the first housing end 109. A retainer 154 can be connected with the first housing end 109. The retainer 154 can be configured to keep the filter screen 152 in an operative position on the first housing end 109. A third seal device 156 can be disposed between the retainer 154 and the filter housing 108. The third seal device 156 can be any sealing device. Illustrative sealing devices include O-rings, gaskets, or similar devices.

A sediment plug 118 can be connected with the second housing end 110. The sediment plug 118 can be configured to connect with the filter base adapter 120.

Figure 2:
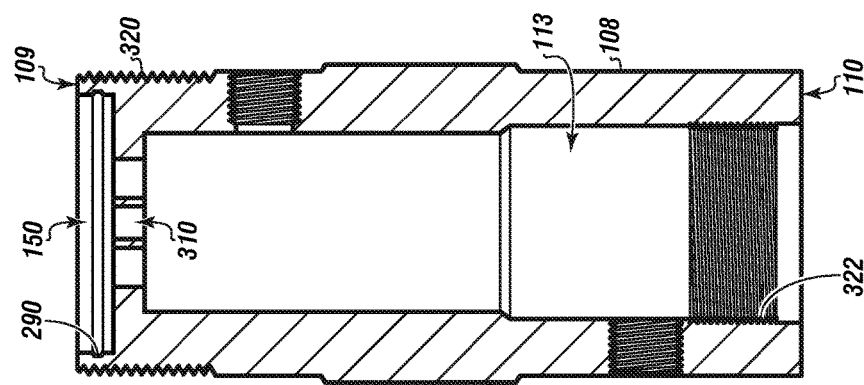
FIG. 2 depicts a cut view of the filter housing of FIG. 3 cut along line A-A.

FIG. 2 depicts a cut view of a filter housing cut along line A-A shown in FIG. 3. FIG. 3 depicts the outside of the filter housing according to one or more embodiments. FIG. 4 depicts a detailed view of a retainer configured to snap into the filter housing of FIG. 3.

The filter housing 108 can have a gripping area 206 or flat portion. The gripping area 206 can have any shape. For example, the gripping area 206 can have an octagonal shape, hexagonal shape, or the like. The gripping area 206 can be designed to allow a tool to engage it, allowing the tool to be used to rotate the filter housing 108.

The filter housing 108 can have a filter screen receiver 150 formed on the first housing end 109. The filter screen receiver 150 can have a first connection member 290 for connecting with the retainer 154. The first connection member 290 can be anything configured to connect with the retainer. Exemplary first connection members can be a lip, a groove, a snap ring, a set screw, a groove, threads, or the like.

The first housing end 109 can have one or more holes 310 formed through it. The one or more holes 310 can allow fluid to flow into the cavity 113, after being filtered by the filter screen. The first housing end 109 can have outer threads 320. The outer threads can be configured to connect the filter housing 108 with a pipeline. The second housing end 110 can have inner threads 322.

The retainer 154 can fit within the filter screen receiver 150, and a second connection member 410 can cooperate with the first connection member 290 to secure the retainer 154 within the filter screen receiver 150. The second connection member 410 can be anything configured to connect with the second connection member. Illustrative second connection members can include holes, indents, threads, grooves, lips, or the like.

The retainer 154 can also include a seal groove 420. In embodiments, the retainer 154 can also house a secondary coupon 131 for pipeline analysis prior to filtering of solids. In embodiments, the secondary coupon 131 can be held in place by a retainer structure 155. The retainer structure 155 can be any means known to persons having ordinary skill in the art. Shown here is a stem on which the secondary coupon 131 can be snapped.

FIG. 5 depicts the device for holding a coupon and collecting a sample of a fluid installed on a pipeline according to one or more embodiments.

The device 100 can be connected with a pipeline 510. For example, the first housing end can be optionally connected with a connector 500 that is connected with the pipeline 510. For example, an isolation valve 540 can be located between the connector 500 and the pipeline 510.

The second housing end 110 can be distal from the pipeline 510. The device 100 can be located on the pipeline 510 at a six o'clock location. The device 100 can collect fluid for sampling from the pipeline 510. The location of the device 100 can allow for the collection of fluids that provide an accurate indication of solids in the fluid. Weighing the coupon prior to installation and after a period of service can provide an indication of deterioration of the pipeline.

A valve 530 can be operatively connected with device 100. The valve 530 can be opened to allow fluid to drain from the cavity. The fluid can be used for sampling, measuring, or analysis. A ventilation valve 531 can be connected with the device 100, allowing for venting as fluid is drained from the cavity.

While these embodiments have been described with emphasis on the embodiments, it should be understood that within the scope of the appended claims, the embodiments might be practiced other than as specifically described herein.

What is claimed is:

1. A device for holding a coupon and collecting a sample of a fluid, wherein the device is for use in a pipeline, and wherein the device comprises:
    a. a filter housing comprising a cavity;
    b. a coupon operatively disposed within the cavity;
    c. a screen aligned with the coupon to prevent solids from contacting the coupon;
    d. a filter cap connected with a first end of the screen;
    e. a filter base adapter connected with a second end of the screen, wherein the filter base adapter is also connected with an end of the coupon;
    f. a filter screen on a first housing end;
    g. a retainer connected with the first housing end, wherein the retainer does not comprise an opening through the retainer, the retainer is configured to keep the filter screen in an operative position on the first housing end, and the retainer is sealed closed with the first housing end; and
    h. a sediment plug connected with a second housing end, wherein the sediment plug is configured to connect with the filter base adapter.

2. The device for holding a coupon and collecting a sample of a fluid of claim 1, further comprising a first opening formed through a side of the filter housing on an upper portion thereof, wherein the first opening is configured to provide ventilation, wherein a second opening is formed through a side of the filter housing on a lower portion thereof, and wherein the is configured to allow fluid to drain out of the housing.

3. The device for holding a coupon and collecting a sample of a fluid of claim 2, further comprising a valve in fluid communication with the device.

4. The device for holding a coupon and collecting a sample of a fluid of claim 1, further comprising a first seal device disposed between the filter cap and the screen.

5. The device for holding a coupon and collecting a sample of a fluid of claim 4, wherein the first seal device is an O-ring.

6. The device for holding a coupon and collecting a sample of a fluid of claim 1, further comprising a second seal device disposed between the filter base adapter and the screen.

7. The device for holding a coupon and collecting a sample of a fluid of claim 1, further comprising a third seal device disposed between the retainer and the filter housing.

8. The device for holding a coupon and collecting a sample of a fluid of claim 1, further comprising a fourth seal device disposed between the sediment plug and the filter housing.

9. The device for holding a coupon and collecting a sample of a fluid of claim 1, wherein the first housing end is configured to support the filter screen, and wherein one or more holes are formed through the first housing end.

10. The device for holding a coupon and collecting a sample of a fluid of claim 1, further comprising a coupon guard disposed between the screen and the coupon, wherein the coupon guard is connected with the filter base adapter.

11. The device for holding a coupon and collecting a sample of a fluid of claim 10, wherein the coupon guard is nonmetallic.

12. The device for holding a coupon and collecting a sample of a fluid of claim 1, wherein the filter base adapter and the filter cap are nonmetallic.

13. The device for holding a coupon and collecting a sample of a fluid of claim 1, wherein the retainer is configured to seal the first housing end.

14. The device for holding a coupon and collecting a sample of a fluid of claim 1, wherein the retainer further houses a secondary coupon.

\* \* \* \* \*